United States Patent [19]

Talebian et al.

[11] Patent Number: 4,895,935

[45] Date of Patent: Jan. 23, 1990

[54] PLATINUM PHARMACEUTICALS

[75] Inventors: Abdolhossen Talebian, Herndon; Dianna C. Green, Falls Church, both of Va.; Charles F. Hammer, Washington, D.C.; Philip S. Schein, Bryn Mawr, Pa.

[73] Assignee: Georgetown University, Washington, D.C.

[21] Appl. No.: 143,762

[22] Filed: Jan. 14, 1988

Related U.S. Application Data

[63] Continuation-in-part of Ser. No. 74,825, Jul. 17, 1987, abandoned.

[51] Int. Cl.$^4$ .................... C07H 15/00; C07H 23/00
[52] U.S. Cl. ..................................... 536/17.1; 536/121
[58] Field of Search .............................. 536/17.1, 121

[56] References Cited

U.S. PATENT DOCUMENTS 4,284,579 8/1981 Meischen ..................... 260/429 R
4,551,524 11/1985 Kidani ............................... 536/121
4,575,550 3/1986 Totani ................................ 536/121

OTHER PUBLICATIONS

Cisplatin: *Current Status and New Developments,* Stephen K. Carter, Academic Press, 1980, pp. 317–431.
O. Gandolfi et al., "Aminomalonato(1,2-diaminocyclohexane)platinum(II)," *Inorganica Chimica Acta,* vol. 135, pp. 27–31, 1987.
M. P. Hacker et al., "Water-Soluble N-substituted Iminodiacetato(1,2-diaminocyclohexane)-platinum(II) Complexes as Potential Antitumor Agents," *Cancer Research,* vol. 46, pp. 6250–6254, 1986.
L. A. Zwelling, "Cisplatin and New Platinum Analogs," *Cancer Chemotherapy* 7, Ch. 8, pp. 105–122, 1985.

*Primary Examiner*—Johnnie R. Brown
*Assistant Examiner*—Pamela S. Webber
*Attorney, Agent, or Firm*—Wegner & Bretschneider

[57] ABSTRACT

Platinum compounds of the formulae:

$$R_1-NH-\underset{\underset{O}{\|}}{C}-N\begin{pmatrix}S(O)\\ \\ \end{pmatrix}\begin{matrix}(CH_2)_n-\underset{\underset{O}{\|}}{C}-O\\ \\(CH_2)_n-\underset{\underset{O}{\|}}{C}-O\end{matrix}\!\!Pt\!\!\begin{matrix}NH_2R_2\\ \\NH_2R_3\end{matrix}$$

and $$R_1-NH-\underset{\underset{O}{\|}}{C}-NH-\begin{pmatrix}S(O)\\ \\ \end{pmatrix}\begin{matrix}(CH_2)_n-\underset{\underset{O}{\|}}{C}-O\\ \\(CH_2)_n-\underset{\underset{O}{\|}}{C}-O\end{matrix}\!\!Pt\!\!\begin{matrix}NH_2R_2\\ \\NH_2R_3\end{matrix}$$

and $$R_1-NH-\underset{\underset{O}{\|}}{C}-N\begin{pmatrix}S(O)\\ \\ \end{pmatrix}\begin{matrix}\underset{\underset{O}{\|}}{C}-O\\ \\ \underset{\underset{O}{\|}}{C}-O\end{matrix}\!\!Pt\!\!\begin{matrix}NH_2R_2\\ \\NH_2R_3\end{matrix}$$

are disclosed. Compositions containing these compounds and methods of using the same in the treatment of tumors are also discussed.

18 Claims, No Drawings

PLATINUM PHARMACEUTICALS

This application is a continuation-in-part of Ser. No. 074,825, filed July 17, 1987, now abandoned.

BACKGROUND OF THE INVENTION

Platinum anti-cancer agents are known in the literature. One of the most well publicized of the platinum anti-cancer agents is cis-diammine-dichloroplatinum (II), also known as cis-DDP and cisplatin. A discussion of cisplatin and its usefulness in the treatment of various types of cancer, such as testicular carcinoma, bladder cancer, ovarian cancer, and head and neck cancer can be found in Zwelling, *Cancer Chemotherapy*, pp. 105–122 (1985).

Problems arise when such platinum agents are used in cancer treatment however. The toxicity of platinum to the bone marrow and kidneys precludes large sized dosages which can, in effect, render such treatment ineffective. Also, the overall desirability of and confidence in chemotherapy based upon known platinum active ingredients is decreased due to the drastic consequences to bone marrow and kidneys of the use of toxic levels of platinum.

SUMMARY OF THE INVENTION

The present invention is directed toward platinum anti-cancer agents having increased water solubility. Such an increase in water solubility aids the body in passing the platinum out of the system, thus preserving healthy bone marrow and kidneys. The water solubility of the platinum anti-cancer agents is enhanced by the presence of a mono or disaccharide group on the platinum active ingredient compound.

Pharmaceutical compositions containing the active ingredient and methods of treating carcinoma by administering said compositions to patients suffering from carcinoma are also discussed.

DETAILED DESCRIPTION OF THE INVENTION

In a first aspect of the present invention, there is provided a compound of the formula:

$$R_1-NH-\overset{S(O)}{\underset{}{C}}-N\overset{(CH_2)_n}{\underset{(CH_2)_n}{\diagdown}}\overset{\overset{O}{\parallel}}{\underset{\overset{\parallel}{O}}{\diagup}}\overset{C-O}{\underset{C-O}{\diagdown}}Pt\overset{NH_2R_2}{\underset{NH_2R_3}{\diagdown}} \quad (I)$$

wherein n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure or a pharmaceutically acceptable salt thereof.

The symbol "(O)" next to the sulfur atom indicates that an oxygen atom may replace the sulfur atom in the structure of the present invention.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the first aspect of the present invention involves a compound of the formula (I), wherein $R_1$ is a mono or disaccharide or derivative thereof selected from the group consisting of glucose, galactose, mannose, glucosamine and galactosamine and derivatives thereof.

Another preferred embodiment of the first aspect of the present invention involves a compound of formula (I), wherein $R_2$ and $R_3$ are hydrogen.

Still another preferred embodiment of the first aspect of the present invention involves a compound of formula (I), wherein $R_2$ and $R_3$ together are linked to adjacent carbon atoms on a five or six membered ring structure.

Another preferred embodiment of the first aspect of the present invention involves a compound of the formula:

$$R_1-NH-\overset{S(O)}{\underset{}{C}}-N\overset{\diagup}{\underset{\diagdown}{\diagdown}}\overset{\overset{O}{\parallel}}{\underset{\overset{\parallel}{O}}{\diagup}}\overset{C-O}{\underset{C-O}{\diagdown}}Pt\overset{NH_3}{\underset{NH_3}{\diagdown}} \quad (II)$$

and $R_1$ is selected from the group comprising glucose mannose, galactose, glucosamine, galactosamine and derivatives thereof.

Further preferred in a first aspect of the present invention is a compound, wherein the compound is of the formula:

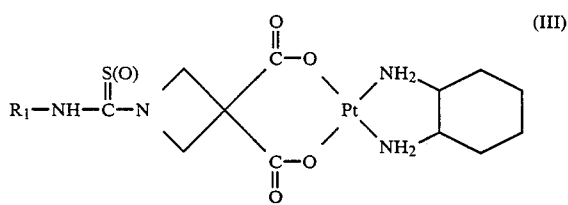

and $R_1$ is selected from the group comprising glucose, mannose, galactose, glucosamine, galactosamine and derivatives thereof.

Additionally preferred in the first aspect of the present invention is a compound, wherein the compound is of the formula:

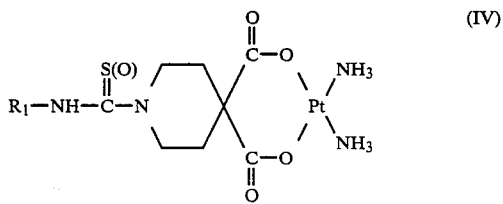

and $R_1$ is selected from the group comprising glucose, mannose, galactose, glucosamine, galactosamine and derivatives thereof.

Another preferred embodiment of the first aspect of the invention is a compound, wherein the compound is of the formula:

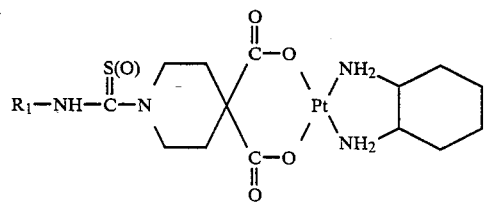

and $R_1$ is selected from the group comprising glucose, mannose, galactose, glucosamine, galactosamine and derivatives thereof.

A second aspect of the present invention involves a compound of the formula:

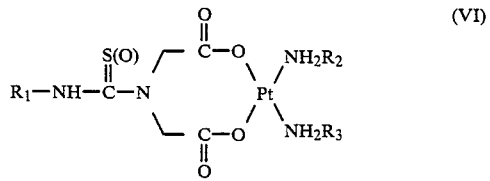

wherein
$R_1$ is a mono or disaccharide or a derivative thereof, $R_2$ and $R_3$ are selected from the group consisting of hydrogen, $C_{1-4}$ alkyl or $R_2$ and $R_3$ or $R_2$ and $R_3$ together are linked to adjacent carbon atoms on a five or six membered ring structure or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated. For example, a 2-(N-acetylamino)- 3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of the second aspect of the present invention involves a compound of the formula (VI), wherein R is a mono or disaccharide or derivative thereof selected from the group consisting of glucose, galactose, mannose, glucosamine and galactosamine and derivatives thereof.

Another preferred embodiment of the second aspect of the present invention involves a compound of formula (VI), wherein $R_2$ and $R_3$ are hydrogen.

Still another preferred embodiment of the second aspect of the present invention involves a compound of formula (VI), wherein $R_2$ and $R_3$ together are linked to adjacent carbon atoms on a five or six membered ring structure.

Further preferred in the second embodiment is a compound, wherein the compound is of the formula:

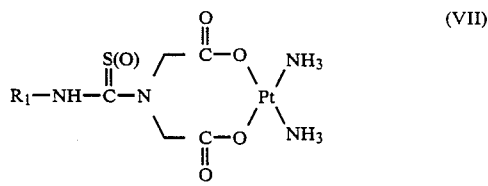

and $R_1$ is selected from the group comprising glucose, mannose, galactose, glucosamine, galactosamine and derivatives thereof.

Additionally preferred in the second embodiment is a compound, wherein the compound is of the formula:

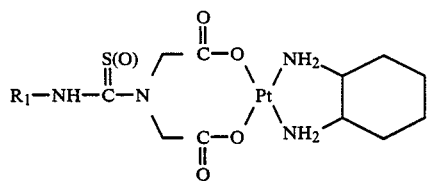

and $R_1$ is selected from the group comprising glucose, mannose, galactose, glucosamine, galactosamine and derivatives thereof.

Also preferred within the second aspect of the present invention is a compound of the formula:

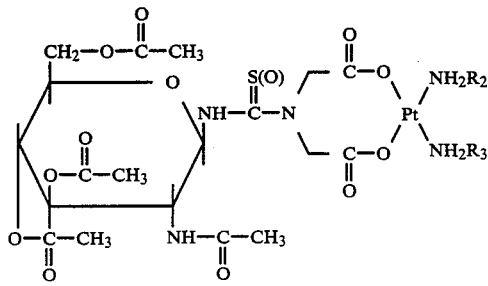

wherein $R_2$ and $R_3$ are as defined above.

In a third aspect of the present invention, there is provided a compound of the formula:

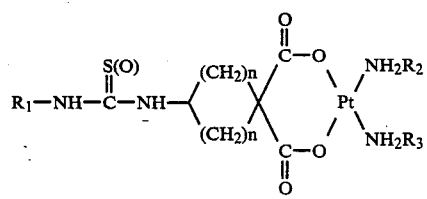

wherein
n is 1 or 2; $R_1$ is a mono or disaccharide or derivative thereof; each of $R_2$ and $R_3$ is independently selected from the group consisting of hydrogen or $C_{1-4}$ alkyl, or $R_2$ and $R_3$ together are linked to adjacent carbon atoms on a five or six membered ring structure
or a pharmaceutically acceptable salt thereof.

As a mono or disaccharide of the present invention there is contemplated any conventional mono or disaccharide. The saccharides may be in pyranosyl or furanosyl form. Preferred form for the saccharides of the present invention is the pyranosyl form. Exemplary monosaccharides are glucose, mannose, galactose, sedoheptulose, sorbose, fructose, ribulose, and xylulose. Exemplary disaccharides are sucrose, lactose, cellobiose, maltose and isomaltose.

As said derivative of the mono or disaccharides there may be mentioned sugar alcohols, deoxy sugars, glyconic acids, glycuronic acids, glycosides, acetyl substituted, amino substituted, N-acetylamino substituted, and the like. Combinations of the various aforementioned substituents on one saccharide are also contemplated For example, a 2-(N-acetylamino)-3,4,6-tri-O-acetyl-2-deoxyglucopyranosyl saccharide moiety is contemplated by the present invention.

As a five or six membered ring structure, there is contemplated a substituted or unsubstituted cyclohexyl or cyclopentyl ring system. The substituents thereon are such that they do not interfere with the anti-cancer activity of the compound. Exemplary of such substituents are $C_{1-4}$ alkyl, hydroxy and the like.

Also contemplated are heterocyclic five or six membered rings having one or more of either nitrogen, oxygen or sulfur or a combination thereof. Exemplary of such rings are furan, pyran, piperidine, and the like.

As a pharmaceutically acceptable salt there is contemplated any salt that is safe for ingestion or injection and that is biologically inert, and hence does not interfere with the active ingredient. As such pharmaceutically acceptable salts may be mentioned sulfates, phosphates and the like.

A preferred embodiment of this aspect involves a compound, wherein said compound is of the formula:

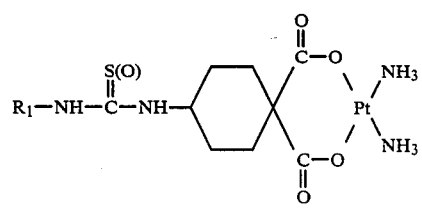

and $R_1$ is selected from the group comprising glucose, mannose, galactose, glucosamine, galactosamine and derivatives thereof.

An additional preferred embodiment of the present invention involves a compound, wherein said compound is of the formula:

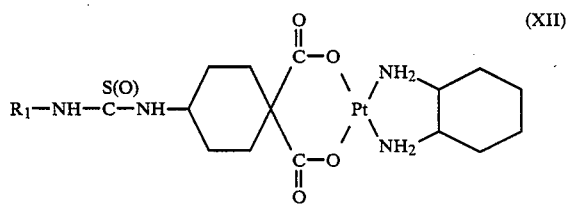

and $R_1$ is selected from the group comprising glucose, mannose, galactose, glucosamine, galactosamine and derivatives thereof.

In accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (I) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anti-cancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, is of formula (I) and is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (I) and is such that $R_2$ and $R_3$ are hydrogen.

Still another preferred composition of the present invention involves a composition, wherein said compound is of formula (I) and is such that $R_2$ and $R_3$ together are linked to adjacent carbon atoms on a five or six membered ring structure.

Additional preferred compositions of the present invention involve compositions, wherein the active compound therein is a compound of formulae (II), (III), (IV), and (V).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (VI) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

A preferred composition of the present invention involves a composition, wherein said compound, i.e. active ingredient, and is of formula (VI) is such that $R_1$ is a mono or disaccharide or derivative thereof selected from the group consisting of glucose, galactose, mannose, glucosamine and galactosamine and derivatives thereof.

Another preferred composition of the present invention involves a composition, wherein said compound is of formula (VI) and is such that $R_2$ and $R_3$ are hydrogen.

Still another preferred composition the present invention involves a composition, wherein said compound is of formula (VI) atoms on a five or six membered ring structure.

Additional preferred compositions of the present invention involve compositions, wherein the active compound therein is a compound of formulae (VII), (VIII) and (IX).

Also, in accordance with the present invention a pharmaceutical composition for the treatment of ailments consisting of testicular cancer, cancer of the ovary, head and neck cancer, cancer of the bladder and cancer of the colon comprising a pharmaceutically effective amount of a compound of the formula (X) and a pharmaceutically acceptable carrier therefor.

The active ingredient is admixed with a pharmaceutically acceptable solid or liquid carrier to allow oral, parenteral, intramuscular or intravenous administration of effective amounts of the pharmaceutical.

As a dosage form for oral delivery there is contemplated any dosage form capable of being delivered orally. That is, tablets, coated tablets, capsules, caplets or any other oral dosage form are contemplated by the present invention.

As said pharmaceutically acceptable inert ingredients there are contemplated pharmaceuticals, carriers, excipients, fillers, etc. which do not interfere with the anticancer activity of said compound.

Fillers such as clays or siliceous earth may be utilized if desired to adjust the size of the dosage form. Further ingredients such as excipients and carriers may be necessary to impart the desired physical properties of the dosage form. Such physical properties are, for example, release rate, texture and size of the dosage form. Examples of excipients and carriers useful in oral dosage forms are waxes such as beeswax, castor wax glycowax and carnauba wax, cellulose compounds such as methylcellulose, ethylcellulose, carboxymethylcellulose, cellulose acetate phthalate, hydroxypropylcellulose and hydroxypropylmethylcellulose, polyvinyl chloride, polyvinyl pyrrolidone, stearyl alcohol, glycerin monostearate, methacrylate compounds such as polymethacrylate, methyl methacrylate and ethylene glycol dimethacrylate, polyethylene glycol and hydrophilic gums.

As an intraperitoneal, intramuscular or intravenous dosage form there is contemplated any dosage form safe for injection purposes and capable of delivering the active platinum containing compound to a patient suffering from ailments consisting of testicular cancer, cancer of the ovary, head and neck cancer, cancer of the bladder and cancer of the colon. Exemplary of such a solution is an isotonic solution. An isotonic solution of the invention may contain in addition to said compound, water and salt, also conventional ingredients such as glucose.

Preferred compositions of the present invention involve compositions, wherein the active compound therein is a compound of formulae (XI) and (XII).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (I) and a pharmaceutically acceptable carrier therefor to a patient suffering from said ailments.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per m$^2$ body surface area of a patient. A preferred dosage of the active compound involves the administration of about 10 to about 200 mg per m$^2$ body surface area of a patient. A more preferred dosage of the active compound involves the administration of about 50 to about 150 mg per m$^2$ body surface area of a patient.

A preferred method of the present invention involves the administration of a compound of formula (I), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (I), wherein said compound is such that $R_2$ and $R_3$ are hydrogen.

A further method of the present invention involves the administration of a compound of formula (I), wherein said compound is such that $R_2$ and $R_3$ together are linked to adjacent carbon atoms on a five or six membered ring structure.

Additional preferred methods of the present invention involve the administration of a compound, wherein the compound therein is a compound of formulae (II), (III), (IV), and (V).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (VI) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per m$^2$ body surface area of a patient. A preferred dosage of the active compound involves the administration of about 10 to about 200 mg per m$^2$ body surface area of a patient. A more preferred dosage of the active compound involves the administration of about 50 to about 150 mg per m$^2$ body surface area of a patient.

A preferred method of the present invention involves the administration of a compound of formula (VI), wherein said compound is such that $R_1$ is a mono or disaccharide or derivative thereof selected from the group consisting of glucose, galactose, mannose, glucosamine and galactosamine and derivatives thereof.

Another preferred method of the present invention involves the administration of a compound of formula (VI), wherein said compound is such that $R_2$ and $R_3$ are hydrogen.

A further method of the present invention involves the administration of a compound of formula (VI), wherein said compound is such that $R_2$ and $R_3$ together are linked to adjacent carbon atoms on a five or six membered ring structure.

Additional preferred methods of the present invention involve administration of compounds, wherein the compound therein is a compound of formulae (VII), (VIII) and (IX).

Further in accordance with the present invention there is provided a method for the treatment of ailments consisting of testicular cancer, cancer of the ovary, head and neck cancer, cancer of the bladder and cancer of the colon comprising administration of a pharmaceutically effective amount of a compound of the formula (X) and a pharmaceutically acceptable carrier therefor to a patient suffering from said ailment.

The administration can occur through oral, intraperitoneal, intramuscular and intravenous routes. Therapeutic treatment profiles can be arranged to administer the compound in accordance with the need of the patient. The need of the patient is dependent on typical factors such as the advancement of the disease, the patient's age, general health, and the like. Daily, weekly, or dosing every two or three weeks are exemplary of possible treatment protocols. With respect to intravenous administration, the compound could be administered constantly. Periods up to 7 days are exemplary of possible intravenous treatment protocols.

Regardless of mode of administration, an exemplary dose of the active compound is from about 1 to about 1000 mg per $m^2$ body surface area of a patient. A preferred dosage of the active compound involves the administration of about 10 to about 200 mg per $m^2$ body surface area of a patient. A more preferred dosage of the active compound involves the administration of about 50 to about 150 mg per $m^2$ body surface area of a patient.

Additional preferred methods of the present invention involve administration of compounds, wherein the compound therein is a compound of formulae (XI) and (XII).

The thio compounds of formula (I) of the present invention may be prepared according to the following reaction scheme:

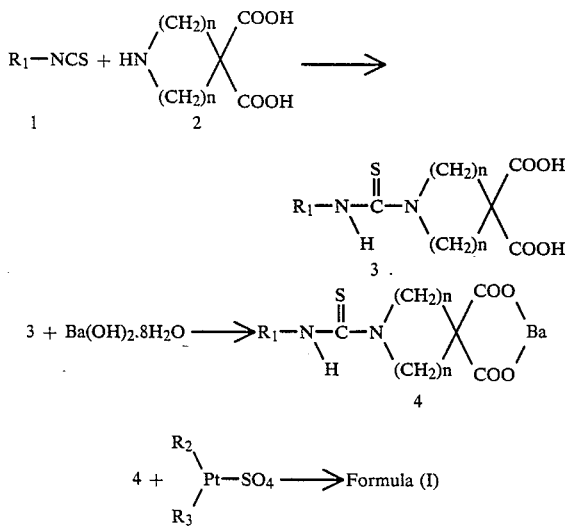

The oxo derivatives can be made in accordance with an analagous method with an $R_1$—NCO starting material.

The compound of formula (VI) may also be made in accordance with the above reaction scheme with the substitution of the following reactant 2 into the first reaction step.

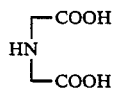

The compounds of the third aspect of the present invention can be prepared according to an analogous reaction mechanism utilizing a cycloalkyl containing starting material.

The following are exemplary of the present invention.

EXAMPLE I 1.2 g of 2-(N-acetylamino)-3,4,6-tri-O-acetyl-2-deoxyglucopyranosyl isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate. The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cis-sulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt-/complex of [[[2-(N-acetylamino)-3,4,6-tri-O-acetyl-2-deoxyglucopyranosyl]amino]thioxomethyl]imino-diacetic acid.

EXAMPLE II

The compound of Example I is admixed with an isotonic solution to produce a dosage form suitable for intravenous administration. 130 mg/$m^2$ body surface area of a patient is administered to said patient through intravenous administration over a period of 24 hours.

EXAMPLE III 1.2 g of tetra-O-acetyl-D-mannopyranosyl-isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography ($CHCl_3$:methanol, 9:1) shows complete disappearance of isothiocyanate. Acetonitrile is removed under reduced pressure and the water layer is basified with saturated sodium bicarbonate and is then extracted with $CHCl_3$. The aqueous layer is acidified with 10% HCl and is extracted with ethylacetate. The ethylacetate layer is backwashed with water and is dried over $Na_2SO_4$. The product is further dried through evaporation in vacuo. A intermediate of formula 3 is formed by recrystallization from ethylether.

0.52 g of this intermediate is admixed with 0.3 g barium hydroxide.$8H_2O$. The resultant is added to 0.4 grams of cis-sulfato-diammine-platinum(II) which is already in solution with 20 ml of water This mixture is stirred at room temperature for 2 hours. Next the barium sulfate is filtered off, and the resulting filtrate is evaporated under reduced pressure to yield a diammine-platinum(II) salt/complex of tetra-O-acetyl-D-mannopyranosyl-amino-thioxomethyl-imino-diacetic acid.

EXAMPLE IV

The compound of Example III is admixed with an isotonic solution to produce a dosage form suitable for intramuscular administration. 80 mg/$m^2$ body surface area of a patient is administered to said patient through intramuscular administration daily.

EXAMPLE V 1.2 g of tetra-O-acetyl-D-galactopyranosyl-isothiocyanate in 5 ml acetonitrile is added to a solution of 0.413 g of iminodiacetic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cyclohexane-1,2-diammine-N,N'-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of tetra-O-acetyl-galactopyranosyl-amino-thioxomethyl-imino-diacetic acid.

EXAMPLE VI

The compound of Example V is admixed with an isotonic solution to produce a dosage form suitable for intraperitoneal administration. 100 mg/m$^2$ body surface area of a patient is administered to said patient through intraperitoneal administration weekly.

EXAMPLE VII 1.2 g of 3,4,6-tri-O-acetyl-2-(N-acetylamino)-2-deoxy-alpha-D-glucopyranosyl-isothiocyanate in 5 ml acetonitrile is added to a solution of 0.413 g of iminodiacetic acid and 1.12 ml of N,N-diisoppropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide. 8H$_2$O. The resultant is added to 0.4 grams of cis-sulfato-amino-methylamino-N,N'-platinum(II) which is already in solution with 20 ml of water. This mixture is stirred at room temperature for 2 hours. Next the barium sulfate is filtered off, and the resulting filtrate is evaporated under reduced pressure to yield a amino-methylamino-N,N'-platinum(II) salt/complex of [[[3,4,6-tri-O-acetyl-2-(N-acetylamino)-2-deoxy-alpha-D-glucopyranosyl]amino]thioxomethyl]imino diacetic acid.

EXAMPLE VIII

The compound of Example VII is admixed with an hydroxypropylcellulose to form a dosage form suitable for oral administration. 120 mg/m$^2$ body surface area of a patient is administered to said patient through oral administration daily.

EXAMPLE IX 1.2 g of 3,4,6-tri-O-acetyl-2-(N-acetylamino)-2-deoxy-alpha-D-galactopyranosyl-isothiocyanate in 5 ml acetonitrile is added to a solution of 0.413 g of 4-amino-1,1-cyclohexanedicarboxylic acid and 1.12 ml of diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cis-sulfato-cyclopentane-1,2-diammine-N,N'-platinum(II) which is already in solution with 20 ml of water. This mixture is stirred at room temperature for 2 hours. Next the barium sulfate is filtered off, and the resulting filtrate is evaporated under reduced pressure to yield a cyclopentane-1,2-diammine-platinum(II) salt/complex of 4-[[[3,4,6-tri-O-acetyl-2-(N-acetylamino)-2-deoxy-alpha-D-galactopyranosyl]amino]thioxomethyl]-1,1-cyclohexanedicarboxylic acid.

EXAMPLE X

The compound of Example IX is admixed with an isotonic solution to produce a dosage form suitable for intravenous administration 150 mg/m$^2$ body surface area of a patient is administered to said patient through intravenous administration over a period of 24 hours.

EXAMPLE XI 1.2 g of 2-(N-acetylamino)-3,4,6-tri-O-acetyl-2-deoxyglucopyranosyl isothiocyanate in 5 ml acetonitrile is added to a solution of 0.413 g of 3,3-trimethyleneimino dicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cis-sulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O-acetyl-2-deoxyglucopyranosyl-amino-thioxomethyl-3,3-trimethyleneimino-dicarboxylic acid.

EXAMPLE XII

The compound of Example XI is admixed with an isotonic solution to produce a dosage form suitable for intramuscular administration. 50 mg/m$^2$ body surface area of a patient is administered to said patient through intramuscular administration daily.

EXAMPLE XIII 1.2 g of tetra-O-acetyl-glucopyranosyl-isothiocyanate in 5 ml acetonitrile is added to a solution of 0.413 g of 4-amino-1,1-cyclohexanedicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide 8H$_2$O. The resultant is added to 0.4 grams of cis-sulfato-(cyclohexane-1,2-diammine-N,N')-platinum(II) which is already in solution with 20 ml of water. This mixture is stirred at room temperature for 2 hours. Next the barium sulfate is filtered off, and the resulting filtrate is evaporated under reduced pressure to yield a cyclohexane-1,2-diammine-platinum(II) salt/complex of 4-[[(tetra-O-acetyl-alpha-D-glucopyranosyl)amino]thioxomethyl]amino]-1,1-cyclohexanedicarboxylic acid.

EXAMPLE XIV

The compound of Example XIII is admixed with an isotonic solution to produce a dosage form suitable for intraperitoneal administration. 150 mg/m$^2$ body surface area of a patient is administered to said patient through intraperitoneal administration every 3 weeks.

EXAMPLE XV 1.2 g of 2-(N-acetylamino)-3,4,6-tri-O-acetyl-2-deoxyglucopyranosyl isothiocyanate in 5 ml acetonitrile is added to a solution of 0.413 g of 3,3-trimethyleneiminodicarboxylic acid and 1.12 ml of diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cis-sulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of 2-(N-acetylamino)-3,4,6-tri-O-acetyl-2-deoxyglucopyranosyl-amino-thioxomethyl-3,3-trimethyleneimino-dicarboxylic acid.

EXAMPLE XVI

The compound of Example XV is admixed with glycerin monostearate to produce a dosage form suitable for oral administration. 70 mg/m$^2$ body surface area of a patient is administered to said patient through oral administration daily.

EXAMPLE XVII 1.2 g of tetra-O-acetyl-galactopyranosyl-isothiocyanate in 5 ml acetonitrile is added to a solution of 0.413 g of 3,3-trimethyleneiminodicarboxylic acid and 1.12 ml of N,N-diisopropylethylamine in 25 ml of a water-acetonitrile mixture (1:1 V/V). The resulting mixture is stirred until thin layer disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide. 8H$_2$O. The resultant is added to 0.4 grams of cis-sulfato-diammine-platinum(II) which is already in solution with 20 ml of water. This mixture is stirred at room temperature for 2 hours. Next the barium sulfate is filtered off, and the resulting filtrate is evaporated under reduced pressure to yield a diammino-platinum(II) salt/complex of [[[tetra-O-acetyl-galactopyranosyl]amino]thioxomethyl]-3,3-trimethyleneiminodicarboxylic acid.

EXAMPLE XVIII

The compound of Example XVII is admixed with glycerin monostearate to produce a dosage form suitable for oral administration. 70 mg/m$^2$ body surface area of a patient is administered to said patient through oral administration daily.

EXAMPLE XIX 1.2 g of tetra-O-acetyl-glucopyranosyl isothiocyanate in 5 ml acetonitrile is added to a solution of 0.413 g of 4,4-piperidinedicarboxylic acid and 1.12 ml of N,N-diisopropylethylamine in 25 ml of a water-acetonitrile mixture (1:1 V/V). The resulting mixture is stirred until thin layer chromatography (CHCl$_3$:methanol, 9:1) shows complete disappearance of isothiocyanate. Acetonitrile is removed under reduced pressure and the water layer is basified with saturated sodium bicarbonate and is then extracted with CHCl$_3$. The aqueous layer is acidified with 10% HCl and is extracted with ethylacetate. The ethylacetate layer is backwashed with water and is dried over Na$_2$SO$_4$. The product is further dried through evaporation in vacuo. A intermediate of formula 3 is formed by recrystallization from ethylether.

0.52 g of this intermediate is admixed with 0.3 g barium hydroxide.8H$_2$O. The resultant is added to 0.4 grams of cis-sulfato-cyclohexane-1,2-diammine-platinum(II) which is already in solution with 20 ml of water. This mixture is stirred at room temperature for 2 hours. Next the barium sulfate is filtered off, and the resulting filtrate is evaporated under reduced pressure to yield a 1,2-cyclohexane-diammino-platinum(II) salt/complex of 4-[[[(tetra-O-acetyl-glucopyranosyl)amino]thioxomethyl]amino]-4,4-piperidinedicarboxylic acid.

EXAMPLE XX

The compound of Example XV is admixed with hydroxypropylcellulose to produce a dosage form suitable for oral administration. 100 mg/m² body surface area of a patient is administered to said patient through oral administration daily.

EXAMPLE XXI

The cyclohexane-1,2-diammine-platinum(II) salt of 2-(acetylamino)-3,4,6-tri-O-acetyl-2-deoxy-glucopyranosyl-amino-thioxomethyl-imino diacetic acid and cisplatin were tested against murine P388 leukemia. The murine P388 leukemia system is known to be sensitive to cisplatin. The leukemia was maintained intraperitoneally in female DBA/2 mice.

Prior to administration, cisplatin was dissolved in ethanol. The solution was then adjusted to 5% ethanol, 95% sterile water. The cyclohexane-1,2-diammine-platinum(II) salt of 2-(acetylamino)-3,4,6-tri-O-acetyl-2-deoxyglucopyranosylamino-thioxomethyl-imino diacetic acid was dissolved in sterile water at 4 degrees celsius immediately prior to administration.

Each compound was administered intraperitoneally to groups of $CD2F_1$ male mice on day 1 after intraperitoneal implantation of $1 \times 10^6$ P388 leukemia cells. P388 antileukemic activity for each compound was assessed by mean survival days and percentage increased life span (% ILS).

ILS is calculated as follows:

$$\% \, ILS = (T-C)/C \times 100$$

wherein T is the mean survival days of the treated mice and C is the mean survival days of the untreated mice. The results of the experimentation are shown in the following table.

TABLE 1

| Compound | Dose | % ILS | Mean Survival (days) |
|---|---|---|---|
| cisplatin | 10 mg/kg | 83 | 17.4 |
| invention | 100 mg/kg | 80 | 17.1 |

What is claimed is:

1. A compound of the formula:

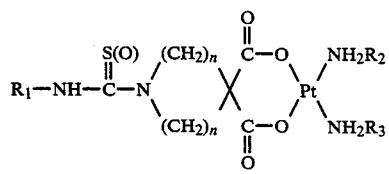

wherein
n is 1 or 2; $R_1$ is a mono or disaccaride which has a five or six membered ring component selected from the group consisting of pyranosyl, furanosyl, sugar alcohols, deoxysugars, glyconic acids, glycuronic acids and glycosides, which can be substituted by acetyl, amino or N-acetylamino; each of $R_2$ and $R_3$ is independently selected from the group consisting of hydrogen of $C_{1-4}$ alkyl, or $R_2$ and $R_3$ together are linked to adjacent carbon atoms on a five or six membered ring structure or a pharmaceutically acceptable salt thereof.

2. A compound of claim 1, wherein $R_1$ is a mono or disaccharide selected from the group consisting of glucose, galactose, mannose, glucosamine and galactosamine and derivatives thereof.

3. A compound of claim 1, wherein $R_2$ and $R_3$ are hydrogen.

4. A compound of claim 1, wherein $R_2$ and $R_3$ together $R_2$ and $R_3$ are linked to adjacent carbon atoms on a five or six membered ring structure.

5. A compound of the formula:

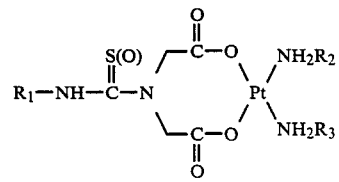

wherein
$R_1$ is a mono or disaccharide which has a five or six membered ring component selected from the group consisting of pyranosyl, furanosyl, sugar alcohols, deoxysugars, glyconic acids, glycuronic acids and glycosides, which can be substituted by acetyl, amino or N-acetylamino, $R_2$ and $R_3$ are selected from the group consisting of hydrogen, $C_{1-4}$ alkyl or $R_2$ and $R_3$ or $R_2$ and $R_3$ together are linked to adjacent carbon atoms on a five or six membered ring structure or a pharmaceutically acceptable salt thereof.

6. A compound of claim 5, wherein $R_1$ is a mono or disaccharide or derivative thereof selected from the group consisting of glucose, galactose, mannose, glucosamine and galactosamine.

7. A compound of claim 5, wherein $R_2$ and $R_3$ are hydrogen.

8. A compound of claim 5, wherein $R_2$ and $R_3$ together $R_2$ and $R_3$ are linked to adjacent carbon atoms on a five or six membered ring structure.

9. A compound of claim 1, wherein the compound is of the formula:

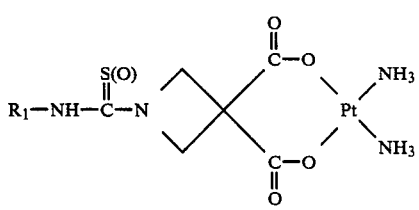

and $R_1$ is selected from the group comprising glucose, mannose, galactose, glucosamine, galactosamine.

10. A compound of claim 1, wherein the compound is of the formula:

[Structure: R₁—NH—C(=S(O))—N bonded to a cyclobutane-like ring with two C(=O)—O groups coordinated to Pt with two NH₂ ligands attached to a cyclohexane ring]

and R₁ is selected from the group comprising glucose, mannose, galactose, glucosamine, galactosamine.

11. A compound of claim 1, wherein the compound is of the formula:

[Structure: R₁—NH—C(=S(O))—N-piperidine-like ring with two C(=O)—O groups coordinated to Pt(NH₃)₂]

and R₁ is selected from the group comprising glucose, mannose, galactose, glucosamine, galactosamine.

12. A compound of claim 1, wherein the compound is of the formula:

[Structure: R₁—NH—C(=S(O))—N-piperidine ring with two C(=O)—O groups coordinated to Pt with diaminocyclohexane]

and R₁ is selected from the group comprising glucose, mannose, galactose, glucosamine, galactosamine.

13. A compound of claim 5, wherein the compound is of the formula:

[Structure: R₁—NH—C(=S(O))—N with two CH₂—C(=O)—O groups coordinated to Pt(NH₃)₂]

and R₁ is selected from the group comprising glucose, mannose, galactose, glucosamine, galactosamine.

14. A compound of claim 5, wherein the compound is of the formula:

[Structure: R₁—NH—C(=S(O))—N with two CH₂—C(=O)—O groups coordinated to Pt with diaminocyclohexane]

and R₁ is selected from the group comprising glucose, mannose, galactose, glucosamine, galactosamine.

15. A compound of claim 5, wherein the compound is of the formula:

[Structure: acetylated sugar ring with NH—C(=S(O))—N-CH₂-C(=O)—O groups coordinated to Pt(NH₂R₂)(NH₂R₃)]

wherein R₂ and R₃ are as defined above.

16. A compound of the formula:

$$R_1-NH-\overset{S(O)}{\underset{\|}{C}}-N\begin{array}{c}(CH_2)_n-\overset{O}{\underset{\|}{C}}-O\\(CH_2)_n-\overset{\|}{\underset{O}{C}}-O\end{array}X\begin{array}{c}NH_2R_2\\Pt\\NH_2R_3\end{array}$$

wherein n is 1 or 2; R₁ is a mono or disaccharide which has a five or six membered ring component selected from the group consisting of pyranosyl, furanosyl, sugar alcohols, deoxysugars, glyconic acids, glycuronic acids and glycosides, which can be substituted by acetyl, amino or N-acetylamino; each of R₂ and R₃ is independently selected from the group consisting of hydrogen or $C_{1-4}$ alkyl, or R₂ and R₃ together are linked to adjacent carbon atoms on a five or six membered ring structure or a pharmaceutically acceptable salt thereof.

17. A compound of claim 16, wherein said compound is of the formula:

[Structure: R₁—NH—C(=S(O))—NH-cyclohexane with two C(=O)—O groups coordinated to Pt(NH₃)₂]

and R₁ is selected from the group comprising glucose, mannose, galactose, glucosamine, galactosamine.

18. A compound of claim 16, wherein said compound is of the formula:

[Structure: R₁—NH—C(=S(O))—NH-cyclohexane with two C(=O)—O groups coordinated to Pt with diaminocyclohexane]

and R₁ is selected from the group comprising glucose, mannose, galactose, glucosamine, and galactosamine.

* * * * *